US012607618B2

(12) United States Patent
Mezghani et al.

(10) Patent No.: US 12,607,618 B2
(45) Date of Patent: Apr. 21, 2026

(54) SYSTEM FOR AUTOMATED LEGACY DRILL CUTTING SAMPLES DIGITIZATION

(71) Applicant: SAUDI ARABIAN OIL COMPANY, Dhahran (SA)

(72) Inventors: Mokhles M. Mezghani, Dhahran (SA); Mustafa Ali H. Al Ibrahim, Safwa (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 293 days.

(21) Appl. No.: 18/305,878

(22) Filed: Apr. 24, 2023

(65) Prior Publication Data

US 2024/0353388 A1 Oct. 24, 2024

(51) Int. Cl.
*G01N 1/00* (2006.01)
*G01N 33/24* (2006.01)
(Continued)

(52) U.S. Cl.
CPC ....... *G01N 33/24* (2013.01); *G01N 35/00732* (2013.01); *G01N 35/0099* (2013.01);
(Continued)

(58) Field of Classification Search
CPC ............. G01N 33/24; G01N 35/00732; G01N 35/0099; G01N 35/04; G01N 2035/00742;
(Continued)

(56) References Cited

U.S. PATENT DOCUMENTS 2,470,743 A * 5/1949 Hochgesang ............ G01V 5/12
378/171
5,161,409 A 11/1992 Hughes et al.
(Continued)

FOREIGN PATENT DOCUMENTS

CA 2638405 A1 12/2009
CN 103104294 B 5/2015
(Continued)

OTHER PUBLICATIONS

Ville Hakala, "Autosampler: A new automated drill cuttings sampling system", Mine On-Line Service Ltd; Feb. 24, 2010; pp. 1-3 (3 pages).
(Continued)

*Primary Examiner* — Robert R Raevis
(74) *Attorney, Agent, or Firm* — Osha Bergman Watanabe & Burton LLP

(57) ABSTRACT
A modular system provides automated legacy drill cutting samples digitization. The system includes a central processing unit, at least one robotic arm, a conveyor, and a retractable stand. The robotic arm, which is controlled by the central processing unit, opens drill cutting samples already bagged and stored in a laboratory. The conveyor transports the drill cutting samples between a plurality of stations that include an extractor, a digitizer, and a packager. The extractor extracts the drill cutting samples; the digitizer performs a plurality of measurements on the extracted samples using one or more measuring sensors attached to the retractable stand; and the packager labels and packs the extracted samples into a collection box.

18 Claims, 7 Drawing Sheets

(51) Int. Cl.

| | |
|---|---|
| *G01N 35/00* | (2006.01) |
| *G01N 35/04* | (2006.01) |
| *G06V 30/10* | (2022.01) |

(52) U.S. Cl.
CPC ... *G01N 35/04* (2013.01); *G01N 2035/00742* (2013.01); *G06V 30/10* (2022.01)

(58) Field of Classification Search
CPC .............. G01N 1/28; G01N 2001/002; G01N 2001/005; G01N 2001/025; G01N 2035/00861; G01N 2203/0284; G01N 35/10; G01N 2001/005; G06V 30/10
USPC ...... 73/152.01, 152.03, 152.04, 863, 863.01, 73/864.31; 166/250.01; 175/40, 46, 48, 175/207; 378/1, 6, 44–50; 438/125–134; 198/339.1, 418–418.3, 502.1
See application file for complete search history.

(56) References Cited

U.S. PATENT DOCUMENTS

| | | | |
|---|---|---|---|
| 12,012,852 B1 * | 6/2024 | Tonner ................. | E21B 21/066 |
| 2005/0082468 A1 | 4/2005 | Zamfes | |
| 2012/0234360 A1 | 9/2012 | Snape et al. | |
| 2014/0048972 A1 | 2/2014 | Gottlieb | |
| 2017/0043965 A1 | 2/2017 | Blaine et al. | |
| 2019/0212282 A1 | 7/2019 | Reiderman | |

| | | | |
|---|---|---|---|
| 2020/0018161 A1 | 1/2020 | Stepanov et al. | |
| 2021/0208089 A1 | 7/2021 | Segal et al. | |
| 2021/0255353 A1 | 8/2021 | Mezghani et al. | |
| 2022/0156429 A1 | 5/2022 | Gan et al. | |
| 2022/0268153 A1 | 8/2022 | Mezghani et al. | |

FOREIGN PATENT DOCUMENTS

| | | | |
|---|---|---|---|
| CN | 212985148 U | | 4/2021 |
| CN | 113008644 A | | 6/2021 |
| CN | 114252333 A | | 3/2022 |
| EP | 3156587 A1 | | 4/2017 |
| KR | 20220119392 | * | 8/2022 |
| WO | 2012/100283 A1 | | 8/2012 |
| WO | 2018076006 A1 | | 4/2018 |
| WO | 2020180405 A1 | | 9/2020 |
| WO | 2022032057 A1 | | 2/2022 |
| WO | 2022/180438 A1 | | 9/2022 |

OTHER PUBLICATIONS

International Search Report issued for corresponding interntional patent application No. PCT/US2024/025919, mailed Jul. 3, 2024 (6 pages).
Written Opinion issued for corresponding interntional patent application No. PCT/US2024/025919, mailed Jul. 3, 2024 (10 pages).
International Preliminary Report on Patentability issued in Application No. PCT/US2024/025919, mailed on Oct. 16, 2025 (9 pages).

* cited by examiner

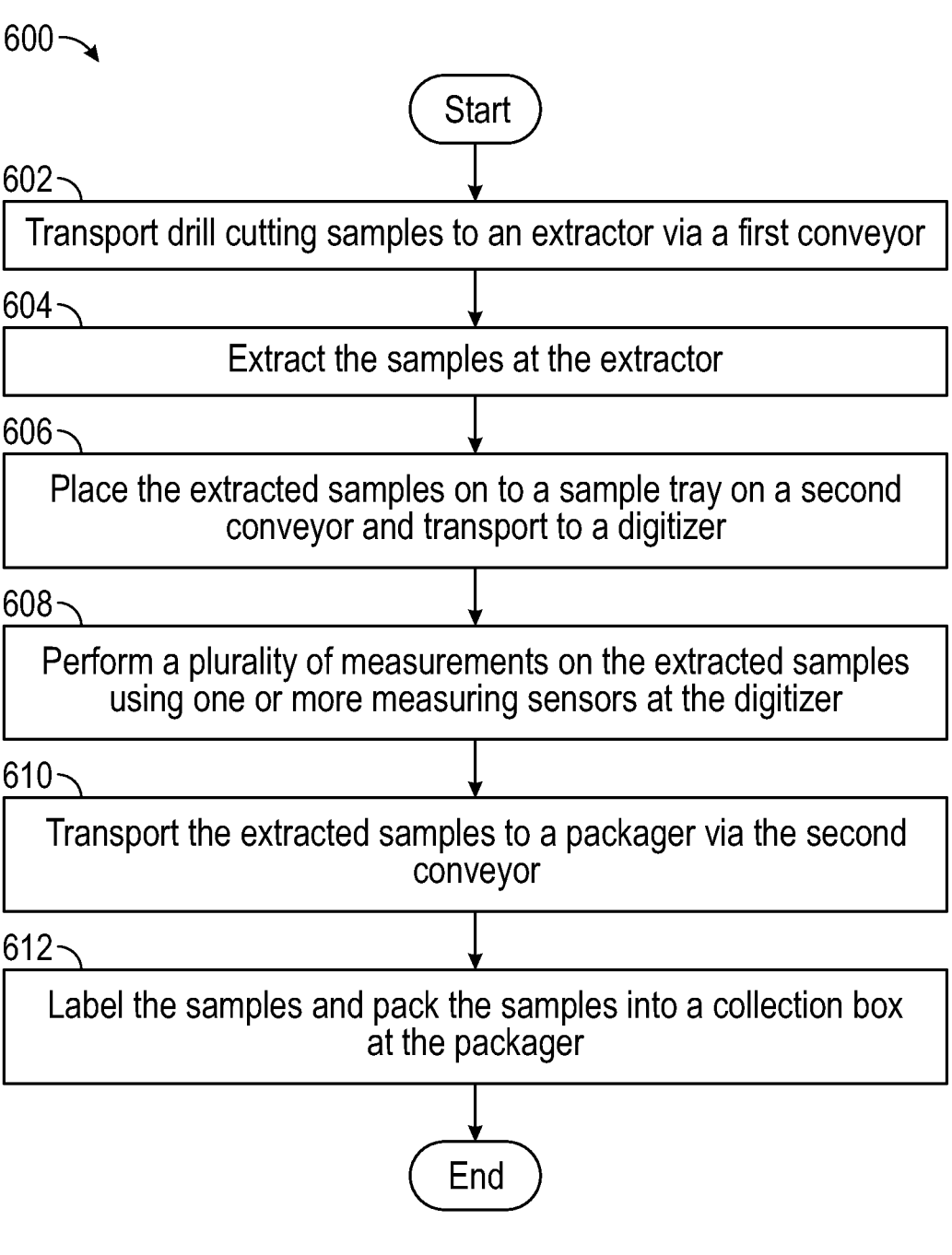

600

Start

602

Transport drill cutting samples to an extractor via a first conveyor

604

Extract the samples at the extractor

606

Place the extracted samples on to a sample tray on a second conveyor and transport to a digitizer

608

Perform a plurality of measurements on the extracted samples using one or more measuring sensors at the digitizer

610

Transport the extracted samples to a packager via the second conveyor

612

Label the samples and pack the samples into a collection box at the packager

End

FIG. 6

SYSTEM FOR AUTOMATED LEGACY DRILL CUTTING SAMPLES DIGITIZATION

BACKGROUND

Drill cutting samples are rock chips collected during a well drilling process. They represent different formations traversed by a drilling bit. Commonly, they are mainly physical sources of rocks available for subsurface data. They are commonly collected at uniform depth intervals (e.g., every 10 feet) providing valuable information from surface to total depth of a well. Samples are traditionally cleaned, packaged in paper envelopes or vials, labeled, and stored for future studies. Examination and quantitative analysis are performed on subsamples as needed.

Considering the footage drilled over the decades, the amount of drill cutting samples collected over the last few decades is large (e.g., in the millions). Accordingly, there is a need for a complete integrated system for extracting, analyzing, and packaging drill cutting samples to maximize the utilization of these samples.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a modular system and methods to automate legacy drill cutting samples digitization.

In one or more embodiments, a modular system for automated legacy drill cutting samples digitization includes a central processing unit; at least one robotic arm controlled by the central processing unit, the at least one robotic arm being configured to open legacy drill cutting samples already bagged and stored in a laboratory; a conveyor configured to transport drill cutting samples between a plurality of stations; and a retractable stand. The plurality of the stations includes an extractor configured to extract the drill cutting samples received via the conveyor, wherein extracted samples are placed onto a sample tray on the conveyor via the at least one robotic arm; a digitizer configured to receive the sample tray via the conveyor, to perform a plurality of measurements on the extracted samples using one or more measuring sensors attached to the retractable stand; and a packager configured to label and pack the extracted samples into a collection box via the at least one robotic arm. The retractable stand configures the one or more measuring sensors for an optimum position to perform the plurality of measurements via the central processing unit.

In one or more embodiments, in the system, a database operably coupled to the central processing unit via a network. The digitizer stores the plurality of the measurements with metadata in the database via the central processing unit. The at least one robotic arm is configured with at least one of an air hose, a water hose, a clasp, a vacuum suction cup, and a cutter. The at least one robotic arm is guided by guiding cameras with RGB video feeds and depth sensors via the central processing unit. The extractor comprises a second camera that reads sample information from envelopes in which they are received and sends the sample information to the digitizer via the central processing unit. A fixed stand is used for a specific sensor to measure the samples. The one or more measuring sensors are activated when the sample tray is reached to the retractable stand via one or more guiding cameras and the central processing unit. The sample information includes at least one of a field name, a well number, a lateral number, an estimated interval sample depth, a collection date, and a time.

In one or more embodiments, in the system, the one or more measuring sensors are brightfield high resolution digital cameras. The one or more sensors are portable x-ray fluorescence and ultraviolet cameras. Multiple sensors are attached to multiple stands. A label is in a form of a passive radio frequency identification device (RFID). A chip id of the RFID is appended to the metadata.

In one or more embodiments, a method for digitizing legacy drill cutting samples includes transporting the legacy drill cutting samples to an extractor via a first conveyor; extracting the legacy drill cutting samples at the extractor; placing the extracted samples on to a sample tray on a second conveyor; transporting the extracted samples to a digitizer via the second conveyor; performing a plurality of measurements on the extracted samples via one or more measuring sensors at the digitizer; transporting the extracted samples to a packager via the second conveyor; and labeling and packing the extracted samples into a collection box at the packager. In the method, a retractable stand, at the digitizer, configures the one or more measuring sensors for an optimum position to perform the plurality of measurements.

Other aspects and advantages of the claimed subject matter will be apparent from the following description and the appended claims.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the disclosed subject matter to the particular forms disclosed, but on the contrary, the intention is to cover all modifications, equivalents, and alternatives falling within the spirit and scope of the disclosed subject matter as defined by the appended claims.

BRIEF DESCRIPTION OF DRAWINGS

Specific embodiments of the disclosed technology will now be described in detail with reference to the accompanying figures. Like elements in the various figures are denoted by like reference numerals for consistency. The advantages and features of the present invention will become better understood with reference to the following more detailed description taken in conjunction with the accompanying drawings in which:

FIG. 6 illustrates is a flowchart of a method for automated legacy drill cutting samples digitization, in accordance with one or more embodiments of the disclosure.

DETAILED DESCRIPTION

Figure 1:
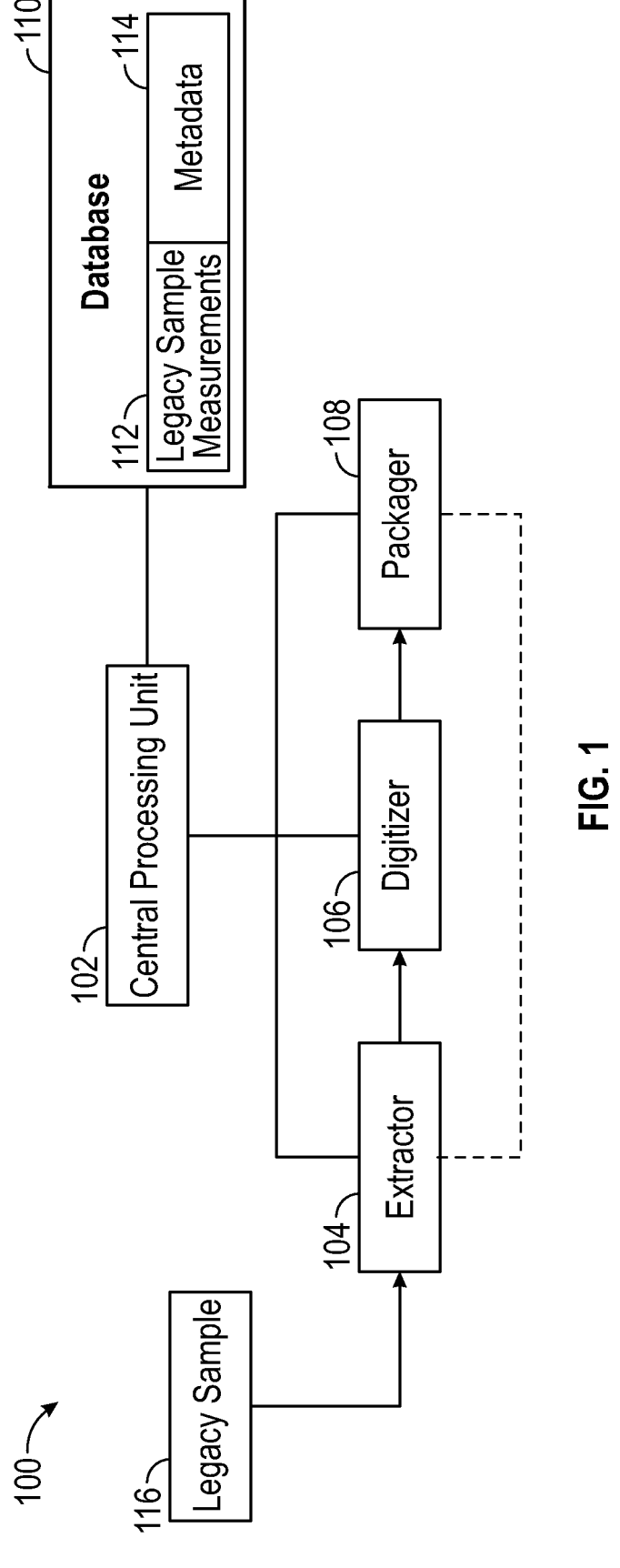
FIG. 1 illustrates a block diagram of an exemplary modular system for automated legacy drill cutting samples digitization, in accordance with one or more embodiments of the disclosure.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-7s, any component described regarding a figure, in various embodiments disclosed herein, may be equivalent to one or more like-named components described with regard to any other figure. For brevity, descriptions of these components will not be repeated regarding each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a wellbore" includes reference to one or more of such wellbores.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims may not be introduced, it would be apparent to one of ordinary skill that the subject matter of the dependent claims directed to one or more embodiments may be combined with other dependent claims.

Drill cutting samples are rock chips collected during a well drilling process. They represent different formations traversed by a drilling bit. Commonly, they are mainly physical sources of rocks available for subsurface data. They are commonly collected at uniform depth intervals (e.g., every 10 feet) providing valuable information from surface to total depth of a well. Samples are traditionally cleaned, packaged in paper envelopes or vials, labeled, and stored for future studies. Examination and quantitative analysis are performed on subsamples as needed.

Considering the footage drilled over the decades, the amount of drill cutting samples collected over the last few decades is large (e.g., in the millions). To maximize the utilization of this large dataset, digitization of these samples through imaging and physical measurements are being utilized to create digital replicas. This invention discloses a system to automate digitization of legacy drill cutting samples.

In one aspect, embodiments disclosed herein relate to a system and a method to automate digitization of legacy drill cutting samples. Embodiments of the present disclosure may provide at least one of the following advantages. Embodiments of the present disclosure provide a way to digitize large amounts of drill cutting samples already bagged and stored in a laboratory to maximize their use. These digitized drill cutting samples allow consistent and accurate measurements that contribute to successful exploration and development operations. Further, embodiments of the present disclosure provide high throughput needed in large scale digitization operations to increase efficiency.

FIG. 1 illustrates a block diagram 100 of an exemplary modular system for automated legacy drill cutting samples digitization. The block diagram 100 depicts a central processing unit 102, an extractor 104, a digitizer 106, a packager 108, a database 110, and a legacy sample 116. The database 110 includes legacy sample measurements 112 and metadata 114. The extractor 104, the digitizer 106, and the packager 108 can be operated independently or as a whole. That is, the extractor 104, the digitizer 106, and the packager 108 may be integrally formed, or may be separate operational modules. The extractor 104, the digitizer 106, and the packager 108 are arranged in a sequential manner, and are connected to the central processing unit 102 to coordinate activities. While not depicted in FIG. 1, one or more robotic arms are used to perform various processes within the extractor 104, the digitizer 106, and the packager 108.

The extractor 104, the digitizer 106, the packager 108, and the central processing unit 102 are operably coupled via an ethernet (i.e., 10/100/1000 Base-T) or a wireless network (i.e., Wi-Fi, 4G, 5G, etc.) to transfer data and action requests. A virtual data connection between the extractor 104 and the packager 108 is facilitated by the central processing unit 102. For example, a legacy sample bag contains texts showing sample information (i.e., well name and sample depth). This sample information is read via a camera, and is parsed using optical character recognition (OCR) at the extractor 104. The parsed information is sent to the packager 108 via an ethernet, which will be printed on a label for a sample package.

The extractor 104 extracts a drill cutting sample from an envelope or a container box. The digitizer 106 measures the drill cutting sample and stores measured data. The packager

108 packs the drill cutting sample into a storage envelope or a storage container. For example, suppose that the legacy sample 116 needs to be digitized. First, the legacy sample 116 is transported to the extractor 104. The extractor 104 extracts a drill cutting sample from the legacy sample 116 in an envelope, and the extracted drill cutting sample is transported to the digitizer 106. At the digitizer 106, the drill cutting sample is measured, and the measurements of the drill cutting sample are stored in the database 110 as the legacy sample measurements 112 with metadata 114. Once digitization of the drill cutting sample is complete, the drill cutting sample is transported to the packager 108. The packager 108 packages the drill cutting sample for a physical storage. Additional details of the extractor 104, the digitizer 106, and the packager 108 are described herein below with respect to FIGS. 3, 4 and 5.

In one or more embodiments, the legacy sample 116 and the extracted drill cutting sample may be transported to each stage (e.g., the extractor 104, the digitizer 106, and the packager 108) via one or more conveyors, or one or more robotic arms. The central processing unit 102 may be one or more processors in a personal computer, a workstation, a local server, and a remote server. The database 110 may be one or more storages in a personal computer, a workstation, a local server, or a cloud.

Figure 2:
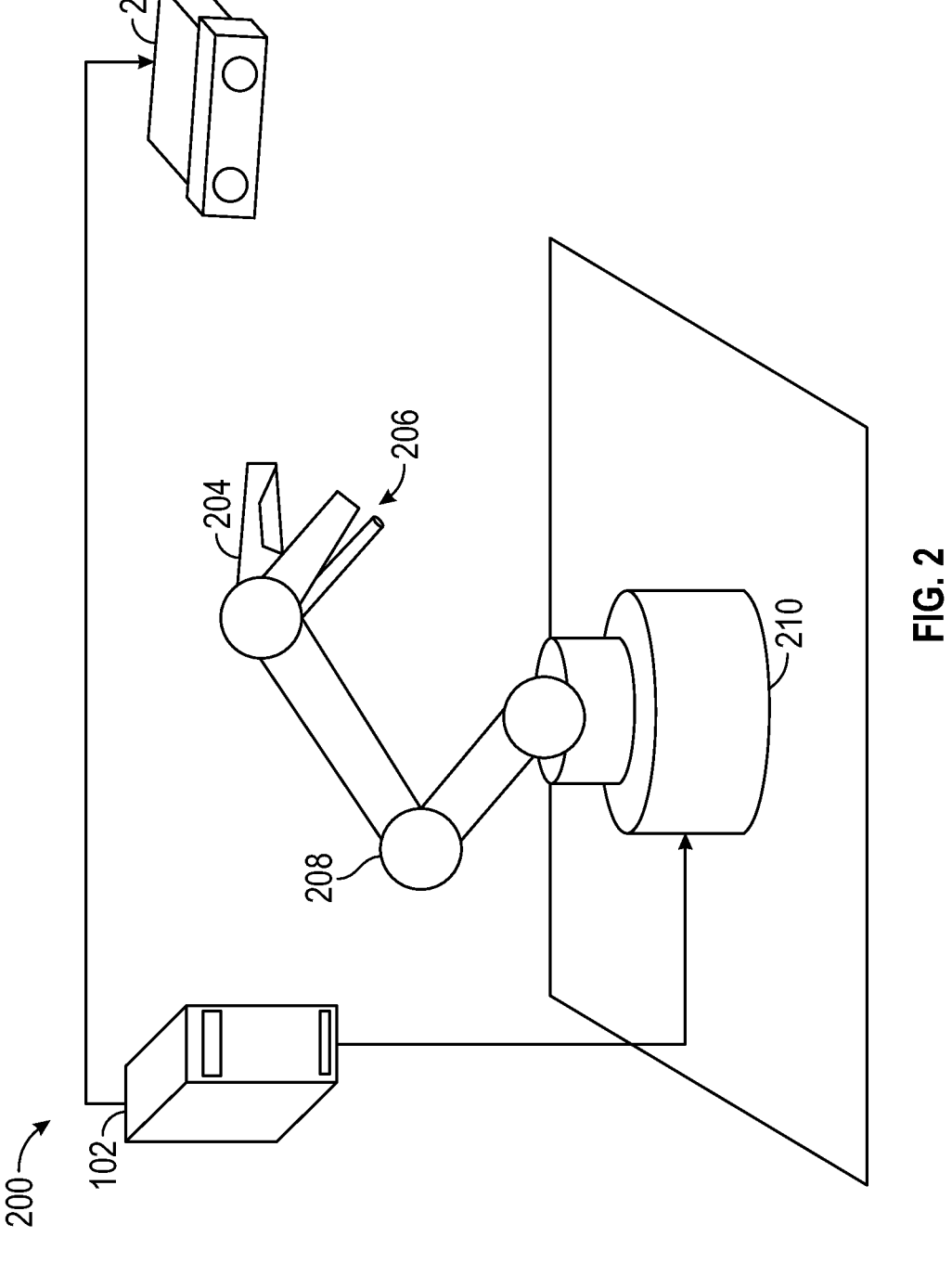
FIG. 2 illustrates an exemplary configuration of a robotic arm, in accordance with one or more embodiments of the disclosure.

FIG. 2 illustrates an exemplary configuration 200 of a robotic arm to perform various processes within at least one of the extractor 104, the digitizer 106, and the packager 108. The configuration 200 depicts a robotic arm 210 configured with an extruding cutter 204, an air/water hose 206, and a rotating hinge 208. The extruding cutter 204 cuts a package open, which contains a drill cutting sample. For example, the robotic arm is configured to automatically open a bagged sample and empty the bagged sample onto a conveyor belt. The air/water hose 206 is used to move a drill cutting sample from one container to the next. The rotating hinge 208 allows the robot arm 210 to move in different directions or angles, or to operate in different heights. The robotic arm 210 is controlled by the central processing unit 102 in FIG. 1, and is guided by one or more cameras with RGB video feed and depth sensors. For example, the one or more cameras with RGB video feed and depth sensors detects an absence or a presence of objects that can be handled by the robot arm 210 (i.e., an old sample bag, a new sample bag, a cutting sample after processing) to trigger robotic arm actions.

In one or more embodiments, the robotic arm 210 may be configured with a clasp or a vacuum suction cup to retrieve and put packaged samples from and into container boxes. In one or more embodiments, a number of robotic arms utilized in a system for automated legacy drill cutting samples digitization may vary based on the configuration of the extractor 104, the digitizer 106, and the packager 108. For example, if the extractor 104, the digitizer 106, and the packager 108 are used in conjunction with each other, a number of robotic arms may be minimized by utilizing ones that are positioned and configured to reach multiple stages. In this case, just one robotic arm, for example, may be utilized.

Figure 3:
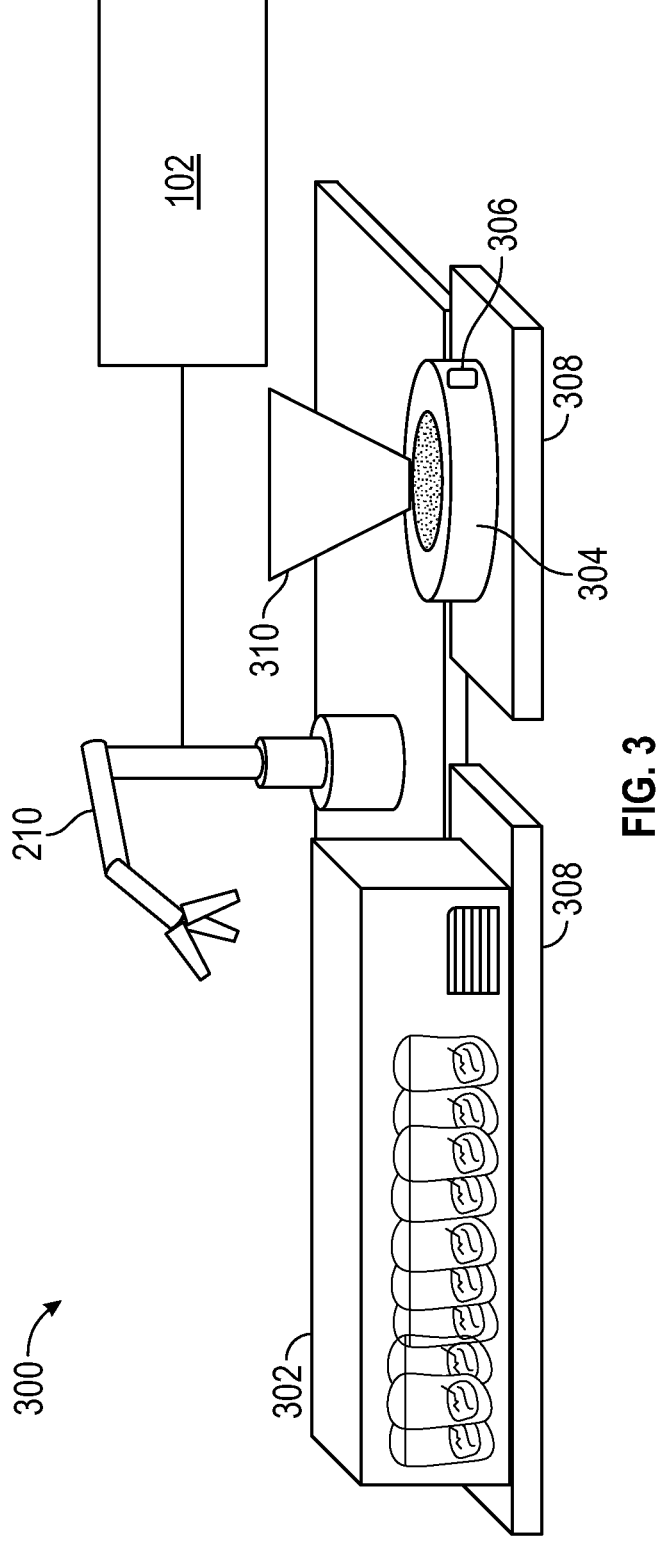
FIG. 3 illustrates an exemplary configuration of an extractor, in accordance with one or more embodiments of the disclosure.

FIG. 3 illustrates an exemplary configuration 300 of the extractor 104 in FIG. 1. The configuration 300 depicts a sample box 302, a sample tray 304, a sample tray holding groove 306, conveyor belts 308, a funnel 310, and a robot arm 210 in FIG. 2 controlled by the central processing unit 102 in FIG. 1. The robot arm 210 may hold and lift the sample tray 304 via the sample tray holding groove 306.

The extractor 300 receives samples in envelopes in the sample box 302 via the conveyer belts 308. The robotic arm 210 extracts one envelope at a time using clasps if the samples are stored in envelopes. The envelope is then opened using the robotic arm 210. For example, a cutting knife or scissors in the robotic arm 210 is used to open envelopes on top of the funnel 310 that leads to the empty sample tray 304. The empty envelope is disposed of in a collection box for recycling. The sample tray 304 is transported to the next stage via the conveyor belts 308.

In one or more embodiments, the sample box 302 may be inserted into the conveyer belt by a human operator, or a robot arm. The robotic arm 210 may extract samples using a vacuum suction cup if the samples are packaged in rigid containers. The robotic arm 210 may be equipped with a vision system to read sample information from the envelope and send the sample information to the subsequent stages (e.g., the digitizer 106 and the digitizer 108). For example, the vision system, which is in communication with the central processing unit 102, uses one or more cameras to view an image of a sample, and processes and interprets the image via computer vision algorithms before sending instructions to the robot arm 210. In one or more embodiments, the sample information includes a well name, a depth, a date, a company name, etc.

Although FIG. 3 depicts the conveyor belts 308 comprising two separate belts, in one or more embodiments, the convey belts 308 may be one continuous belt or more than two separate belts. Further, although FIG. 3 depicts one robot arm utilized in the extractor 104, more than one robot arm may be utilized in the extractor 104.

Figure 4:
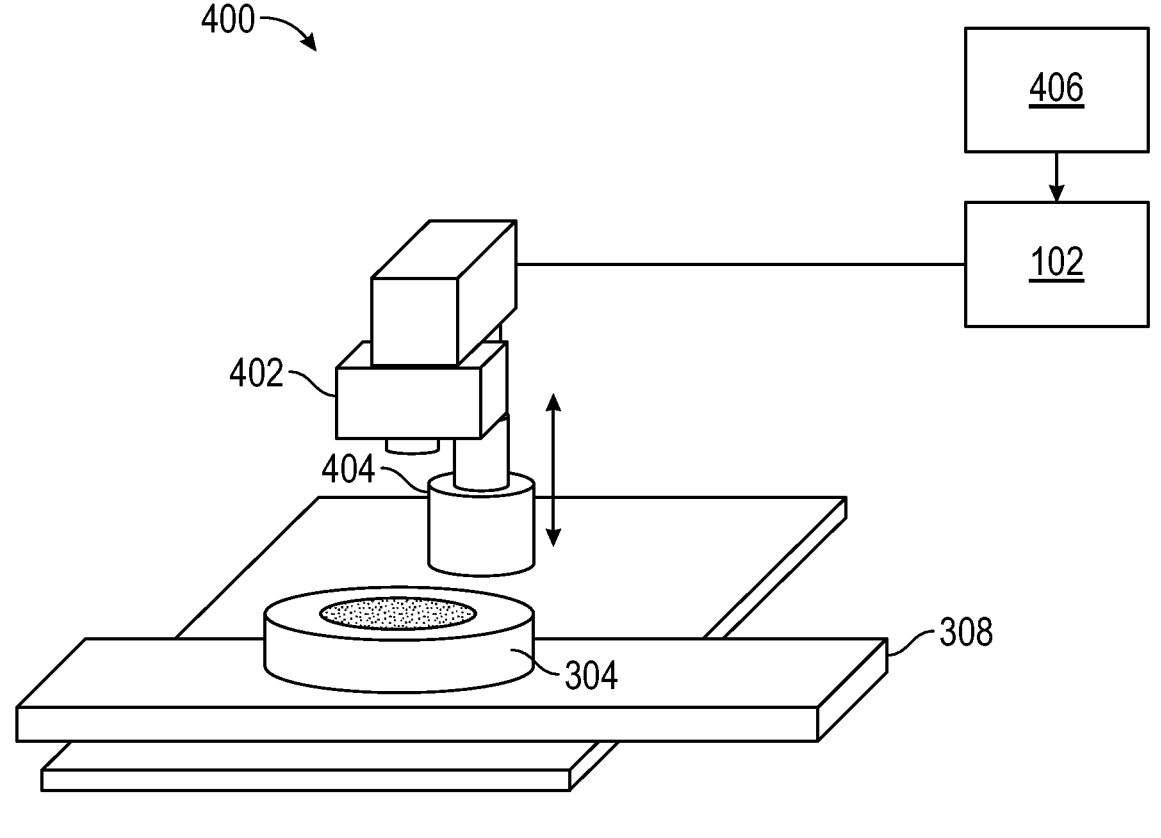
FIG. 4 illustrates an exemplary configuration of a digitizer, in accordance with one or more embodiments of the disclosure.

FIG. 4 illustrates an exemplary configuration 400 of the digitizer 106 in FIG. 1. The configuration 400 depicts a measuring sensor 402 controlled by the central processing unit 102 in FIG. 1, a retractable stand 404, a guiding camera 406, the sample tray 304 in FIG. 3, and the conveyor belts 308. In one or more embodiments, the guiding camera 406 is a low-resolution camera compared to cameras in FIGS. 2 and 3, and is used for activating the measuring sensor 402. The retractable stand 404 allows the measuring sensor 402 to be at its optimum position by adjusting a distance between the sample tray 304 and the measuring sensor 402. The measuring sensor 402 is activated as the sample tray 402 reaches the retractable stand 404. This is determined by the guiding camera 406 in communication with the central processing unit 102. Multiple images at multiple zoom levels are taken during performing measurements. Measured results are transferred to the central processing unit 102 and stored in the database 110 as the legacy sample measurements 112 with the metadata 114. In one or more embodiments, the measured results may depend on the digitization sensor. In this case, for example, the measured results are sample images taken by the measuring sensor 402. Once the measurements are done, the sample tray 304 is transported to a next sensor for another measurement, or a next station via the conveyor belts 308.

Those skilled in the art will appreciate that other digitization sensors may be used to obtain different measured results. For example, additional sensors such as a hyperspectral camera, a gamma ray, etc. may be employed by the system.

In one or more embodiments, the retractable stand 404 may be operably connected to the central processing unit 102 to control the position of the measuring sensor 402. The measured results may depend on sensors used by the digitizer 106. The metadata 114 may include a well name, a sample depth, a date, a company name, etc.

In one or more embodiments, the measuring sensor 402 may a brightfield high-resolution digital camera to capture images of a drill cutting sample on the sample tray 304. The measuring sensor 402 may be a portable (miniature) x-ray fluorescence and ultraviolet cameras, all of which are commonly known in the art and not described herein for the sake of brevity. For the x-ray fluorescence, the measuring sensor 402 is protracted to touch the drill cutting sample in the sample tray 304, and to obtain measurements. For ultraviolet images, the drill cutting sample is moved to a completely closed box to eliminate outside light. The measuring sensor 402 may include an auto focusing lens for high quality images.

In one or more embodiments, a fixed stand may be used instead of the retractable stand 404. A specifically designed stand may be configured based on one or more measuring sensors attached to it. Multiple measuring sensors may be used to measure drill cutting samples. Multiple stands, each with a different measuring sensor, may be used in the digitizer 106.

Although FIG. 4 depicts only one conveyor belt of the conveyor belts 308, in one or more embodiments, multiple conveyor belts may be used. Further, although FIG. 4 depicts no one robot arm utilized in the digitizer 106, one or more robot arms may be utilized in the digitizer 106.

Figure 5:
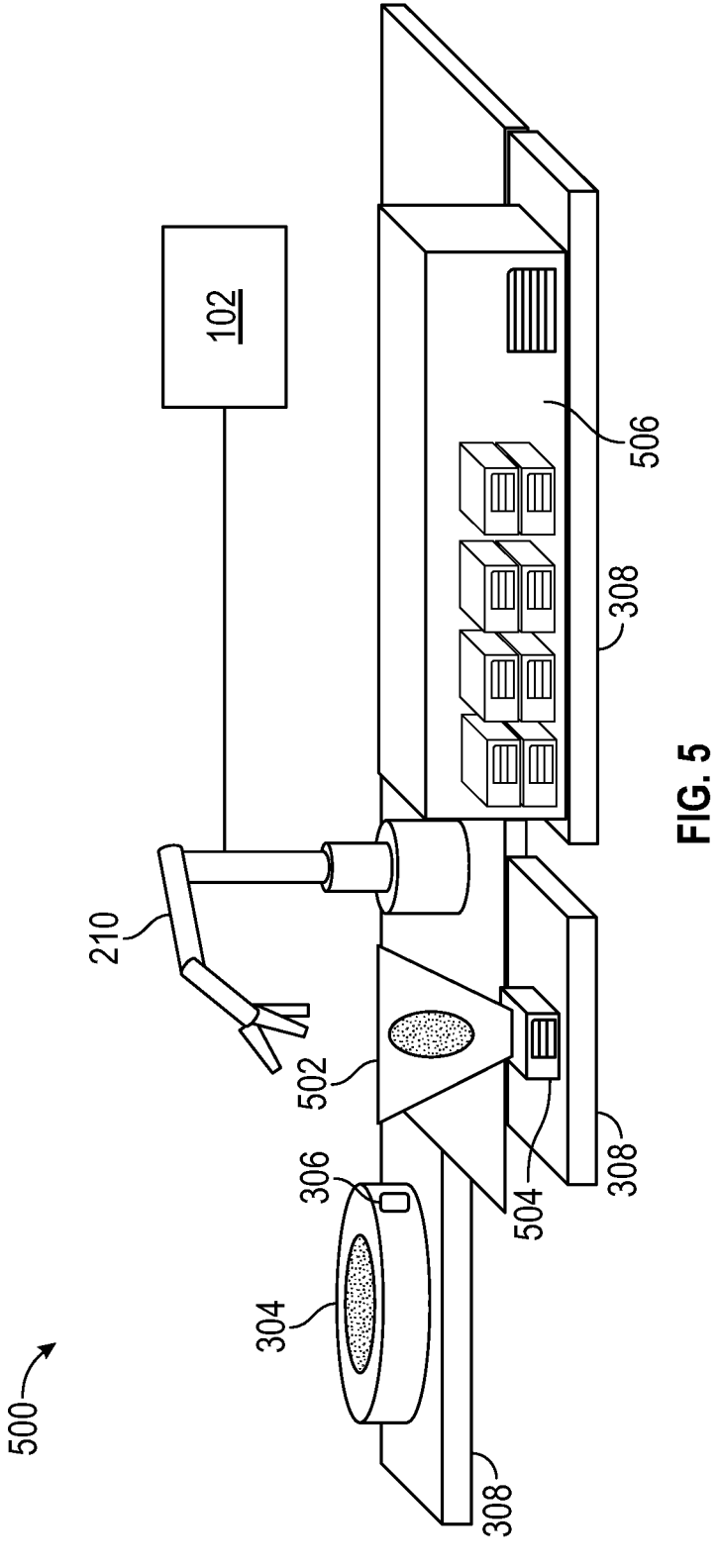
FIG. 5 illustrates an exemplary configuration of a packager, in accordance with one or more embodiments of the disclosure.

FIG. 5 illustrates an exemplary configuration 500 of the packager 108 in FIG. 1. The configuration 500 depicts a funnel 502, a sample package 504, a sample box 506, the robot arm 210 in FIG. 2 controlled by the central processing unit in FIG. 1, the sample tray 304 with the sample tray holding groove 306, and the conveyor belts 308 in FIG. 3.

The packager 108 is responsible for packaging drill cutting samples. An automated labeler (not depicted) creates a label. The label may contain identifying information, which includes at least one of a field name, a well number, a lateral number, an estimated interval sample depth, and collection date and time. The label is glued on the sample package 504 automatically.

After the labeling is complete, a drill cutting sample in the sample tray 304 is picked up by the robot arm 210 via the sample tray holding groove 306, and placed on top of the funnel 502. Then, the robot arm 210 drops the sample into the sample package 504 via the funnel 502. An air/water hose attached to the robotic arms 210 may be used to clean the sample tray 304 to ensure that the sample is thoroughly vacated to the sample package 504. In alternate embodiments, the robot arm may pick up the sample directly. The central processing 102 controls a number of packaged samples deposited in the sample box 506. For example, only a predetermined number of the packaged samples is stored in each sample box 506 (e.g., fifty samples in each box). Once the sample box 506 is full, the sample box 506 is transported to a storage facility or an advanced processing center via the conveyor belts 308.

In one or more embodiments, a label may be in a form of water-resistant physical paper or a passive radio-frequency identification device (RFID). A RFID chip identifier (chip ID) may be appended to the metadata 114 in the database 110. The sample package 504 may be a plastic, paper, or glass bag, or a box. Fifty samples may be packaged in the sample box 506.

Although FIG. 5 depicts one robot arm utilized in the packager 108, in one or more embodiments, any number of robot arms, coordinated by the central processing unit 102, may be utilized in the packager 108.

The detailed workflow of digitizing legacy drill cutting samples is depicted herein with respect to FIG. 6. FIG. 6 illustrates a flowchart of a method for automated legacy drill cutting samples digitization. Method 600 may be performed by processing logic that includes hardware (e.g., circuitry, dedicated logic, programmable logic, microcode, etc.), software (e.g., instructions run on a processing device to perform hardware simulation), or a combination thereof. In one implementation, the method 600 may be performed by the extractor 104, the digitizer 106, and the packager 108 as described with respect to FIG. 1. In describing the method 600, reference is made to FIGS. 1-5 illustrating an implementation. It is noted the example provided in FIGS. 1-5 is meant for illustrative purposes and is not meant to limit the scope disclosed herein.

Initially, at block 602, drill cutting samples are transported to an extractor via a conveyor. In FIG. 3, drill cutting samples 302 are transported to the extractor 102 via one of the conveyor belts 308.

At block 604, the drill cutting samples are extracted at the extractor. In FIG. 3, the drill cutting samples 302 is extracted using the robot arm 210. At block 606, the extracted samples are placed onto a sample tray on a second conveyor and transported to a digitizer. In FIG. 3, the extracted sample is placed on to the sample tray 304 via the funnel 310, and is transported to the digitizer 106 via the other conveyor belt of the conveyor belts 308.

At block 608, a plurality of measurements is performed on the extracted samples using one or more measuring sensors at the digitizer. In FIG. 4, the digitizer 106 performs a plurality of measurements on the extracted samples on the sample tray 304 via the measuring sensor 402 attached to the retractable stand 404.

At block 610, the extracted samples are transported to packager via the second conveyor. At block, 612, the extracted samples are labeled and packed into a collection box at the packager. Then the method 600 ends. In FIG. 5, the packager 108 labels and packs the samples on the sample tray 304 into the sample package 504.

Figure 7:
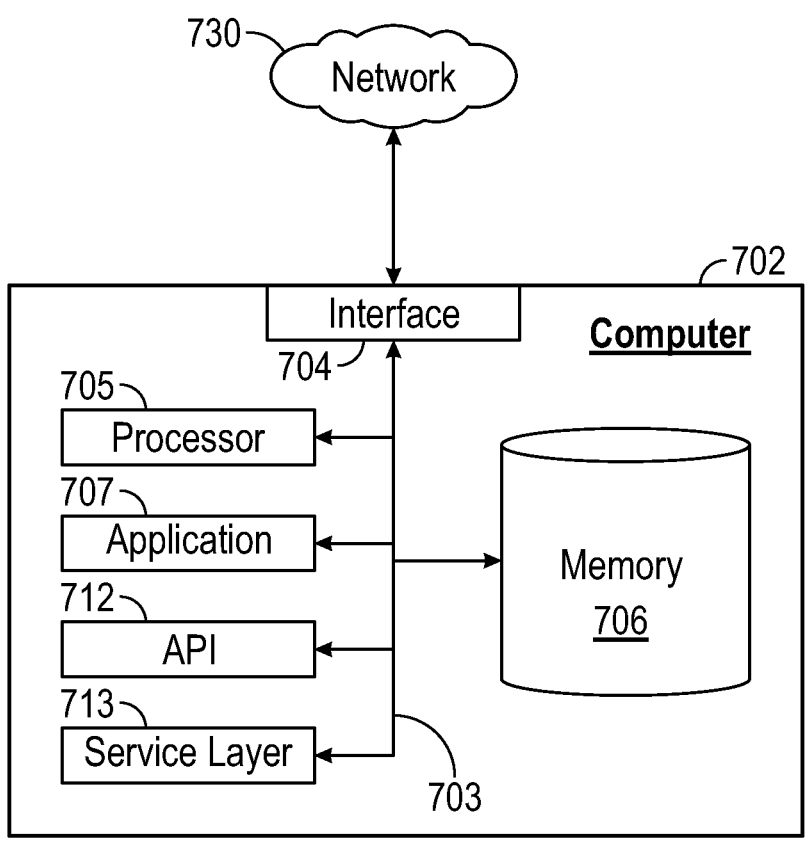
FIG. 7 illustrates a block diagram of an exemplary computer device operating, in accordance with one or more embodiments of the disclosure

FIG. 7 is a block diagram of a computer system 702 configured to provide computational functionalities associated with a method for automated legacy drill cutting samples digitization as described herein.

The illustrated computer system 702 is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer system 702 includes an input device, such as a keypad, keyboard, touch screen, or other device that can accept user information, and an output device that conveys information associated with the operation of the computer system 702, including digital data, visual, or audio information (or a combination of information), or a GUI.

The illustrated computer system 702 is communicably coupled with a network 730 or cloud. In some implementations, one or more components of the computer system 702 are configured to operate within environments, including cloud-computing-based, local, global, or other environment (or a combination of environments).

At a high level, the computer system 702 is an electronic computing device operable to receive, transmit, process, store, or manage data and information associated with the described subject matter. According to some implementations, the computer system 702 also includes or is communicably coupled with an application server, e-mail server, web server, caching server, streaming data server, business intelligence (BI) server, or other server (or a combination of servers) via the network 730.

Each of the components of the computer system 702 communicates using a system bus 703. In some implementations, any or all of the components of the computer system 702, both hardware or software (or a combination of hardware and software), may interface with each other or the interface 704 (or a combination of both) over the system bus 703 using an application programming interface (API) 712 or a service layer 713 (or a combination of the API 712 and service layer 713. The API 712 includes specifications for routines, data structures, and object classes. The API 712 is either computer-language independent or dependent and refers to a complete interface, a single function, or even a set of APIs. The service layer 713 provides software services to the computer system 702 or other components (whether or not illustrated) that are communicably coupled to the computer system 702. The functionality of the computer system 702 is accessible for all service consumers using this service layer. Software services, such as those provided by the service layer 713, provide reusable, defined business functionalities through a defined interface. For example, the interface is software written in JAVA, C++, VB scripts or other suitable language providing generation of keys. While illustrated as an integrated component of the computer system 702, alternative implementations may illustrate the API 712 or the service layer 713 as stand-alone components in relation to other components of the computer system 702 or other components (whether or not illustrated) that are communicably coupled to the computer system 702. Moreover, any or all parts of the API 712 or the service layer 713 are implemented as child or sub-modules of another software module, enterprise application, or hardware module without departing from the scope of this disclosure.

The computer system 702 includes an interface 704. Although illustrated as a single interface 704 in FIG. 7, two or more interfaces 704 are used according to particular needs, desires, or particular implementations of the computer system 702. The interface 704 is used by the computer system 702 for communicating with other systems in a distributed environment that is connected to the network 730. Generally, the interface 704 includes logic encoded in software or hardware (or a combination of software and hardware) and operable to communicate with the network 730 or cloud. More specifically, the interface 704 includes software supporting one or more communication protocols associated with communications such that the network 730 or interface's hardware is operable to communicate physical signals within and outside of the illustrated computer system 702.

Further, the computer system 702 includes at least one computer processor 705. Although illustrated as a single computer processor 705 in FIG. 7, two or more processors are used according to particular needs, desires, or particular implementations of the computer system 702. Generally, the computer processor 705 executes instructions according to a method to digitize drill cutting samples to perform the operations of the computer system 702 and any algorithms, methods, functions, processes, flows, and procedures as described in the instant disclosure to convert unstructured documents to structured documents. Further, the computer processor 705 provides functionality for the central processing unit 102 in FIG. 1.

The computer system 702 also includes a memory 707 that stores instructions and output data for the computer system 702 or other components (or a combination of both)

that is connected to the network 730. In one or more embodiments, the memory 707 may be a non-transitory computer-readable storage medium. For example, the memory 707 stores a method for automated legacy drill cutting samples digitization consistent with this disclosure. Although illustrated as a single memory 707 in FIG. 7, two or more memories are used according to particular needs, desires, or particular implementations of the computer system 702 and the described functionality. While memory 707 is illustrated as an integral component of the computer system 702, in alternative implementations, memory 707 is external to the computer system 702. Memory 707 may provide functionality for the database 110 in FIG. 1.

The application 707 is an algorithmic software engine providing functionality according to particular needs, desires, or particular implementations of the computer system 702, particularly with respect to functionality described in this disclosure. For example, application 707 serves as one or more components, modules, applications, etc. Further, although illustrated as a single application 707, the application 707 is implemented as multiple applications 707 on the computer system 702. In addition, although illustrated as integral to the computer system 702, in alternative implementations, the application 707 is external to the computer system 702.

There are any number of computers associated with, or external to, a computer system containing computer system 702, each computer system 702 communicating over network 730.

In some embodiments, the computer system 702 is implemented as part of a cloud computing system. For example, a cloud computing system includes one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which are performed using one or more Internet connections. More specifically, a cloud computing system may operate according to one or more service models, such as infrastructure as a service (IaaS), platform as a service (PaaS), software as a service (SaaS), mobile "backend" as a service (MBaaS), artificial intelligence as a service (AIaaS), serverless computing, and/or function as a service (FaaS).

For purposes of this disclosure, any element mentioned in the singular also includes the plural.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A modular system for automated digital recording of a plurality of legacy drill cutting samples, the system comprising:

the plurality of legacy drill cutting samples, wherein each legacy drill cutting sample is a geological sample previously collected during a drilling operation, packaged in a legacy storage container, and archived for future research;

a central processing unit (CPU);

at least one robotic arm operably coupled to the CPU;

a plurality of stations operably coupled to the CPU; and a conveyor configured to transport the plurality of legacy drill cutting samples between the plurality of stations;

wherein the plurality of stations comprise:

a sample extractor for removing the legacy drill cutting sample from the legacy storage container, the sample extractor comprising:

a sample tray comprising a holding groove; and a first funnel situated over the sample tray, wherein, for each legacy drill cutting sample of the plurality of legacy drill cutting samples, the sample extractor is configured to:

receive, by the at least one robotic arm, the legacy storage container from the conveyor;

open, by the at least one robotic arm, the legacy storage container over the first funnel such that the legacy drill cutting sample is transferred from the legacy storage container to the sample tray via the first funnel;

transport, by the at least one robotic arm, the sample tray to the conveyor, wherein the at least one robotic arm uses the holding groove to transport the sample tray;

a sample digitizer for digitally recording the legacy drill cutting sample, the sample digitizer comprising:

one or more stands situated to receive the sample tray from the conveyor, wherein each of the one or more stands comprises one or more measuring sensors, wherein, for each legacy drill cutting sample of the plurality of legacy drill cutting samples, the sample digitizer is configured to:

receive, by the one or more stands, the sample tray from the conveyor;

perform a plurality of measurements on the legacy drill cutting sample using the one or more measuring sensors to obtain a plurality of measurement values, wherein the one or more stands comprise a retractable stand configured to adjust a distance between the sample tray and each of the one or more measuring sensors such that each of the one or more measuring sensors is at an optimum position to perform the plurality of measurements;

record the plurality of measurement values into a database operably coupled to the CPU; and transport, by the at least one robotic arm, the sample tray to the conveyor, wherein the at least one robotic arm uses the holding groove to transport the sample tray; and a sample packager for preparing the legacy drill cutting sample for long-term storage, the sample packager comprising:

a long-term sample package configured to store the legacy drill cutting sample, a second funnel situated over the long-term sample package, and a long-term sample box configured to store a plurality of long-term sample packages, wherein, for each legacy drill cutting sample of the plurality of legacy drill cutting samples, the sample packager is configured to:

receive, by the at least one robotic arm, the sample tray from the conveyor;

overturn, by the at least one robotic arm, the sample tray over the second funnel such that the legacy drill cutting sample is transferred from the sample tray to the long-term sample package via the second funnel;

affix, by the at least one robotic arm, an identifying label onto the long-term sample package; and transport, by the at least one robotic arm, the long-term sample package to the long-term sample box.

2. The system according to claim 1, wherein the at least one robotic arm is configured with at least one of an air hose, a water hose, a clasp, a vacuum suction cup, and a cutter.

3. The system according to claim 1, wherein the at least one robotic arm is guided by one or more cameras comprising RGB video feeds and depth sensors.

4. The system according to claim 1, wherein the sample extractor comprises a camera configured to:

scan the legacy storage container to obtain identifying sample information; and transmit the identifying sample information to the sample digitizer and the sample packager.

5. The system according to claim 4, wherein the identifying sample information comprises a sample source, a sample depth, and a sample date.

6. The system according to claim 4, wherein the identifying label is in a form of water-resistant physical paper and comprises the identifying sample information received from the sample extractor.

7. The system according to claim 4, wherein the database further comprises metadata related to the legacy drill cutting sample, wherein the metadata comprises the identifying sample information received from the sample extractor.

8. The system according to claim 7, wherein the metadata further comprises a tag identifier number of a radio frequency identification (RFID) tag.

9. The system according to claim 8, wherein the identifying label is the RFID tag, and wherein the RFID tag comprises the identifying sample information received from the sample extractor.

10. The system according to claim 1, wherein the one or more stands further comprise a fixed stand.

11. The system according to claim 1, wherein the sample digitizer comprises one or more cameras configured to:

activate the one or more measuring sensors based on the one or more stands receiving the sample tray.

12. The system according to claim 1, wherein the one or more measuring sensors comprise a brightfield high resolution digital cameras.

13. The system according to claim 1, wherein the one or more measuring sensors comprise a portable X-ray fluorescence (XRF) device and an ultraviolet cameras.

14. A method for automated digital recording of a plurality of legacy drill cutting samples, the method comprising:

obtaining the plurality of legacy drill cutting samples, wherein each legacy drill cutting sample is a geological sample previously collected during a drilling operation, packaged in a legacy storage container, and archived for future research;

for each legacy drill cutting sample of the plurality of legacy drill cutting samples:

receiving, by at least one robotic arm operably coupled to a central processing unit (CPU), the legacy storage container from a conveyor, wherein the conveyor is configured to transport the plurality of legacy drill cutting samples between a plurality of stations;

opening, by the at least one robotic arm, the legacy storage container over a first funnel situated over a sample tray such that the legacy drill cutting sample is transferred from the legacy storage container to the sample tray via the first funnel, wherein the sample tray comprises a holding groove configured to be used to maneuver the sample tray by the at least one robotic arm;

transporting, by the at least one robotic arm, the sample tray to the conveyor, receiving, by one or more stands, the sample tray from the conveyor, wherein each of the one or more stands comprises one or more measuring sensors;

performing a plurality of measurements on the legacy drill cutting sample using the one or more measuring sensors to obtain a plurality of measurement values, wherein the one or more stands comprise a retractable stand configured to adjust a distance between the sample tray and each of the one or more measuring sensors such that each of the one or more measuring sensors is at an optimum position to perform the plurality of measurements;

recording the plurality of measurement values into a database operably coupled to the CPU; and transporting, by the at least one robotic arm, the sample tray to the conveyor; and receiving, by the at least one robotic arm, the sample tray from the conveyor;

overturning, by the at least one robotic arm, the sample tray over a second funnel situated over a long-term sample package such that the legacy drill cutting sample is transferred from the sample tray to the long-term sample package via the second funnel affixing, by the at least one robotic arm, an identifying label onto the long-term sample package; and transporting, by the at least one robotic arm, the long-term sample package to a long-term sample box, wherein the long-term sample box is configured to store a plurality of long-term sample packages.

15. The method according to claim 14, wherein the one or more measuring sensors comprise a brightfield high resolution digital camera.

16. The method according to claim 14, wherein the one or more measuring sensors comprise a portable X-ray fluorescence (XRF) device and an ultraviolet camera.

17. The method according to claim 14, wherein the database further comprises metadata related to the legacy drill cutting sample, wherein the metadata comprises a sample source, a sample depth, and a sample date.

18. The method according to claim 14, wherein the one or more stands further comprise a fixed stand.

* * * * *